(12) United States Patent
Mou et al.

(10) Patent No.: US 10,837,884 B2
(45) Date of Patent: Nov. 17, 2020

(54) PARTICLE DETECTING MODULE

(71) Applicant: Microjet Technology Co., Ltd., Hsinchu (TW)

(72) Inventors: Hao-Jan Mou, Hsinchu (TW); Chi-Feng Huang, Hsinchu (TW); Yung-Lung Han, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 181 days.

(21) Appl. No.: 16/263,351

(22) Filed: Jan. 31, 2019

(65) Prior Publication Data

US 2019/0331564 A1    Oct. 31, 2019

(30) Foreign Application Priority Data

Apr. 27, 2018    (TW) .............................. 107114583 A

(51) Int. Cl.
*G01N 1/44* (2006.01)
*B01D 53/00* (2006.01)
(Continued)

(52) U.S. Cl.
CPC .............. *G01N 1/44* (2013.01); *B01D 53/005* (2013.01); *G01N 15/0211* (2013.01);
(Continued)

(58) Field of Classification Search
CPC .............. G01N 15/06; G01N 15/0606; G01N 15/0656; G01N 15/1404; G01N 15/1459;
(Continued)

(56) References Cited

U.S. PATENT DOCUMENTS 7,111,496 B1    9/2006 Lilienfeld et al.
10,451,051 B2 *    10/2019 Chen ...................... F04B 53/10
(Continued)

FOREIGN PATENT DOCUMENTS

CN    106574888 A    4/2017
TW    M554535 U    1/2018
TW    M558353 U    4/2018

OTHER PUBLICATIONS

Extended European Search Report for European Application No. 19154731.4, dated Aug. 23, 2019.

*Primary Examiner* — Francis C Gray
(74) *Attorney, Agent, or Firm* — Birch, Stewart, Kolasch & Birch, LLP

(57) ABSTRACT

A particle detecting module includes a main body, a particle monitoring base, an actuator, a heater and a sensor. The main body has a first and a second compartment. The main body has an inlet, a hot gas exhausting opening and an outlet. The inlet and the hot gas exhausting opening are in fluid communication with the first compartment. The outlet is in fluid communication with the second compartment. A communicating opening is communicated with the first and the second compartment. The particle monitoring base is disposed between the first compartment and the supporting partition plate. The first compartment is heated to maintain a monitor standard level of humidity in the first compartment. The sensor is disposed adjacent to the supporting partition plate and located in a monitoring channel of the particle monitoring base, thereby monitoring the gas. The particle detecting module can be applied to a slim portable device.

13 Claims, 10 Drawing Sheets

(51) Int. Cl.
*G01N 15/02* (2006.01)
*G01N 15/06* (2006.01)
*G01N 15/14* (2006.01)
*G01N 33/00* (2006.01)

(52) U.S. Cl.
CPC ..... *G01N 15/0606* (2013.01); *G01N 15/0656* (2013.01); *G01N 15/1404* (2013.01); *G01N 33/0014* (2013.01); *G01N 33/0022* (2013.01); *G01N 33/0073* (2013.01)

(58) Field of Classification Search
CPC ............. G01N 1/44; G01N 2015/0046; G01N 2035/00455; G01N 33/0014; G01N 33/0022; G01N 33/0073; B01D 53/005
See application file for complete search history.

(56) References Cited

U.S. PATENT DOCUMENTS

| | | |
|---|---|---|
| 10,488,305 B2 * | 11/2019 | Miller-Lionberg .......................... G01N 1/2273 |
| 2008/0281528 A1 * | 11/2008 | Relle, Jr. .............. G01N 1/2273 702/19 |
| 2017/0115196 A1 | 4/2017 | Tsuboi et al. |
| 2017/0261260 A1 * | 9/2017 | Chen ..................... F26B 19/005 |
| 2018/0059079 A1 * | 3/2018 | Meng ..................... G01N 15/06 |

* cited by examiner

PARTICLE DETECTING MODULE

FIELD OF THE DISCLOSURE

The present disclosure relates to a particle detecting module, and more particularly to a particle detecting module capable of being applied to a slim portable device for monitoring gas and maintaining a specified level of humidity beneficial to gas monitoring.

BACKGROUND OF THE DISCLOSURE

Suspended particles are solid particles or droplets contained in the air. Since the sizes of the suspended particles are very small, the suspended particles may enter the lungs of the human body through the nasal hair in the nasal cavity easily, thus causing inflammation, asthma or cardiovascular disease in the lungs. If other pollutants are attached to the suspended particles, it will increase the harm to the respiratory system.

Most of the current gas detections are performed at fixed-points, and only the gas information around the gas observation station is measured. The information of the concentration of suspended particles cannot be provided anytime and anywhere. In addition, the detection of suspended particles is difficult to avoid the interference of water vapor. In a high-humidity environment, the suspended particles would be surrounded by water vapor and have larger volume. Under this circumstance, the light transmittance thereof becomes insufficient, and the small water molecules (water droplets) in the air are increased, which will directly affect the accuracy of the detection.

SUMMARY OF THE DISCLOSURE

An object of the present disclosure is to provide a particle detecting module capable of being assembled in a slim portable device for particle monitoring. The particle detecting module firstly inhales gas into a first compartment through an inlet, and then the gas is heated in the first compartment, so that the gas in the first compartment can be maintained at a monitor standard level, thereby enhancing the detecting efficiency of a gas sensor. A main body of the particle detecting module has a monitoring chamber allowing the air to flow in and flow out in one way for detecting. The resonance plate is actuated by the actuator to guide the gas. As a result, the suspended particles outside the slim portable device are really imported to the particle detecting module to be detected, and the object of detecting suspended particles at anytime and anywhere is achieved.

In accordance with an aspect of the present disclosure, a particle detecting module is provided. The particle detecting module includes a main body, a particle monitoring base, an actuator, a heater and a sensor. The interior of the main body is divided into a first compartment and a second compartment by a supporting partition plate. The main body has an inlet, a hot gas exhausting opening and an outlet. The inlet and the hot gas exhausting opening are in fluid communication with the first compartment. The outlet is in fluid communication with the second compartment. The supporting partition plate has a communicating opening in fluid communication between the first compartment and the second compartment. The particle monitoring base is disposed between the first compartment and the supporting partition plate. The particle monitoring base has a monitoring channel, which has an accommodating recess located at one end thereof and in fluid communication with the monitoring channel. The actuator is disposed within the accommodating recess for controlling gas to be introduced from the inlet into the first compartment, transported to the second compartment through the communicating opening, and discharged through the outlet, thereby achieving single-direction gas transportation. The heater is disposed within the first compartment for heating the first compartment to maintain a monitor standard level of humidity within the first compartment. The sensor is disposed adjacent to the supporting partition plate and located in the monitoring channel of the particle monitoring base, thereby monitoring the gas guided into the monitoring channel.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
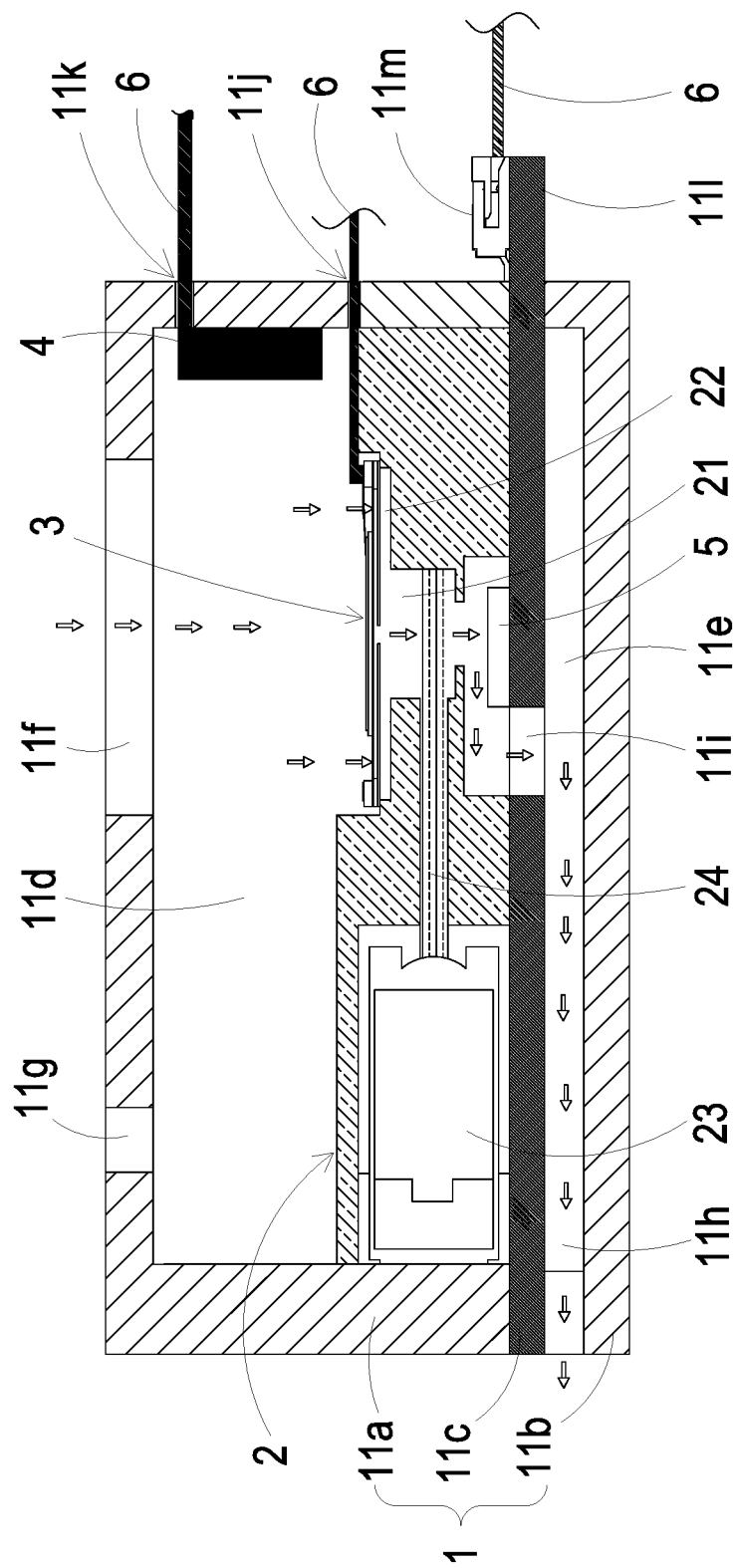
FIG. 1 is a schematic cross-sectional view illustrating a particle detecting module according to an embodiment of the present disclosure.

Please refer to FIG. 1. The present disclosure provides a particle detecting module including at least one main body 1, at least one particle monitoring base 2, at least one actuator 3, at least one heater 4, at least one sensor 5, at least one supporting partition plate 11c, at least one first compartment 11d, at least one second compartment 11e, at least one inlet 11f, at least one hot gas exhausting opening 11g, at least one outlet 11h, at least one communicating opening 11i, at least one monitoring channel 21, at least one accommodating recess 22 and at least one monitor standard level of humidity. The numbers of the main body 1, the particle monitoring base 2, the actuator 3, the heater 4, the sensor 5, the supporting partition plate 11c, the first compartment 11d, the second compartment 11e, the inlet 11f, the hot gas exhausting opening 11g, the outlet 11h, the communicating opening 11i, the monitoring channel 21, the accommodating recess 22 and the monitor standard level of humidity are exemplified by one for each respectively in the following embodiments but not limited thereto. It is noted that each of the main body 1, the particle monitoring base 2, the actuator 3, the heater 4, the sensor 5, the supporting partition plate 11c, the first compartment 11d, the second compartment 11e, the inlet 11f, the hot gas exhausting opening 11g, the outlet 11h, the communicating opening 11i, the monitoring channel 21, the accommodating recess 22 and the monitor standard level of humidity can also be provided in plural numbers.

The present disclosure provides a particle detecting module. Please refer to FIG. 1. According to one embodiment, the particle detecting module includes a main body 1, a particle monitoring base 2, an actuator 3, a heater 4 and a sensor 5. The main body 1 includes a first body 11a, a second body 11b and a supporting partition plate 11c. The first body 11a and the second body 11b are oppositely connected to each other while the supporting partition plate 11c is disposed therebetween, so that the first body 11a and the second body 11b are combined as the main body 1. Meanwhile, the interior of the first body 11a and the second body 11b of the main body 1 is divided into a first compartment 11d and a second compartment 11e by the supporting partition plate 11c. The main body 1 has an inlet 11f, a hot gas exhausting opening 11g and an outlet 11h. In this embodiment, the inlet 11f and the hot gas exhausting opening 11g are both formed on the first body 11a and in fluid communication with the first compartment 11d, while the outlet 11h is formed between the second body 11b and the supporting partition plate 11c to begin fluid communication with the second compartment 11e. In addition, the supporting partition plate 11c has a communicating opening 11i in fluid communication between the first compartment 11d and the second compartment 11e. Thus, within the main body 1, a gas channel is constructed by the inlet 11f, the first compartment 11d, the communicating opening 11i, the second compartment 11e and the outlet 11h for transporting the gas in one-way (as the path shown by the arrows in FIG. 1).

According to the above-mentioned embodiment, the inlet 11f and the hot gas exhausting opening 11g are both disposed on the first body 11a, and the outlet 11h is disposed between the second body 12b and the supporting partition plate 11c. In some other embodiments, the inlet 11f and the hot gas exhausting opening 11g are both disposed between the first body 11a and the supporting partition plate 11c to be in fluid communication with the first compartment 11d, while the outlet 11h is disposed on the second body 11b to be in fluid communication with the second compartment 11e, but not limited thereto. The types of the openings can be varied according to the practical demands.

In the present disclosure, the particle monitoring base 2 is disposed within the first compartment 11d. According to the above-mentioned embodiment, the particle monitoring base 2 is disposed on the supporting partition plate 11c. In some other embodiments, the particle monitoring base 2 may also be disposed adjacent to the supporting partition plate 11c and accommodated within the first compartment 11d. In this embodiment, the particle monitoring base 2 has a monitoring channel 21. A first end of the monitoring channel 21 is directly towards the inlet 11f, so that the gas can be guided from the inlet 11f into the monitoring channel 21 directly without interference. The first end of the monitoring channel 21 also has an accommodating recess 22 in fluid communication with the monitoring channel 21. A second end of the monitoring channel 21 is in fluid communication with the communicating opening 11i of the supporting partition plate 11c.

According to the above-mentioned embodiment, the actuator 3 is disposed within the accommodating recess 22 of the particle monitoring base 2 for drawing the gas inside the first compartment 11d into the monitoring channel 21. The heater 4 is disposed in the first compartment 11d for heating the gas inside the first compartment 11d to maintain the humidity in the first compartment 11d at a monitor standard level. The monitor standard level of the relative humidity is falling within a preferable range that is beneficial to monitor the suspended particles. The water vapor generated as a result of heating the first compartment 11d by the heater 14 is exhausted through the hot gas exhausting opening 11g. The actuator 3 is disposed within the accommodating recess 22 of the particle monitoring base 2 as covering and sealing the accommodating recess 22. The actuator 3 is configured to control the gas to be introduced into the first compartment 11d through the inlet 11f, transported to the second compartment 11e through the communicating opening 11i, and discharged out through the outlet 11h, thereby achieving single-direction gas transportation within the main body 1. The sensor 5 is disposed adjacent to the supporting partition plate 11c and located in the monitoring channel 21 of the particle monitoring base 2, thereby monitoring the gas guided into the monitoring channel 21. As described above, the first end of the monitoring channel 21 is directly towards the inlet 11f, so that the gas guided into the inlet 11f can be directly guided to the monitoring channel 21 without interference. As a result, the process of guiding the gas into the monitoring channel 21 to be measured by the sensor 5 is accelerated, which enhances the working efficiency of the sensor 5. Moreover, after the gas is introduced into the first compartment 11d through the inlet 11f, the gas is heated and dehumidified by the heater 4, so that the humidity of the gas is maintained at the monitor standard level, thereby enhancing the accuracy of the detection of the sensor 5. In some embodiments, the monitor standard level of humidity is in a range between 10% and 40%. In some other embodiments, the monitor standard level of humidity is in a range between 20% and 30%.

According to the above-mentioned embodiment, the particle monitoring base 2 further includes a laser 23 and a beam channel 24. The laser 23 is electrically connected to the supporting partition plate 11c and disposed adjacent to the beam channel 24 for emitting a light beam into the beam channel 24. The beam channel 24 is perpendicularly in communication with the monitoring channel 21 to allow the light beam emitted from the laser 23 to illuminate the monitoring channel 21. When the gas in the monitoring channel 21 is illuminated by the light beam, the suspended particles contained in the gas are illuminated to generate a plurality of scattering light points projected on the sensor 5, and the sensor 5 receives the scattering light points generated by the suspended particles to measure the sizes and the concentrations of the suspended particles. The sensor 5 may be but not limited to a PM 2.5 sensor. After the suspended particles are illuminated by the light beam and the scattering light points are generated, the scattering light points are utilized to calculate the sizes and the concentrations of the suspended particles, so that the concentration of PM 2.5 is detected.

Please refer to FIG. 1 again. The first body 11a of the main body 1 of the particle detecting module has a first connecting perforation 11j provided for a flexible circuit board 6 to penetrate therethrough and connect to the actuator 3. After connecting the flexible circuit board 6 to the actuator 3, the first connecting perforation 11j is sealed by a potting compound to prevent gas from flowing into the first compartment 11d therethrough. The first body 11a further has a second connecting perforation Ilk provided for a flexible circuit board 6 to penetrate therethrough and connect to the heater 4. After connecting the flexible circuit board 6 to the heater 4, the second connecting perforation Ilk is sealed by a potting compound to prevent gas from flowing into the first compartment 11d therethrough. In addition, the supporting partition plate 11c may have an exposed portion 111 penetrated through the main body 1 and extended to an exterior of the main body 1. The exposed portion 111 has a connector 11m. The connector 11m allows the flexible circuit board 6 to be penetrated through so as to connect with the supporting partition plate 11c to provide electric connection and signal connection. The supporting partition plate 11c may be a circuit board. In this embodiment, a humidity detecting device (not shown) is disposed in the first compartment 11d. The humidity detecting device is electrically connected to the heater 4 and is used for detecting the humidity inside the first compartment 11d. When the humidity inside the first compartment 11d, which is detected by the humidity detecting device, is at a level higher than the monitor standard level, an enable signal is transmitted to the heater 4 by the humidity detecting device, and then the heater 4 is enabled to heat the gas in the first compartment 11d for excluding the water vapor. On the other hand, when the humidity inside the first compartment 11d, which is detected by the humidity detecting device, is at a level in a range of or less than the monitor standard level, a disable signal is transmitted to the heater 4 by the humidity detecting device, and then the heater 4 stops heating. In some other embodiments, the humidity detecting device is embedded in the heater 4, but not limited thereto.

Figure 2A:
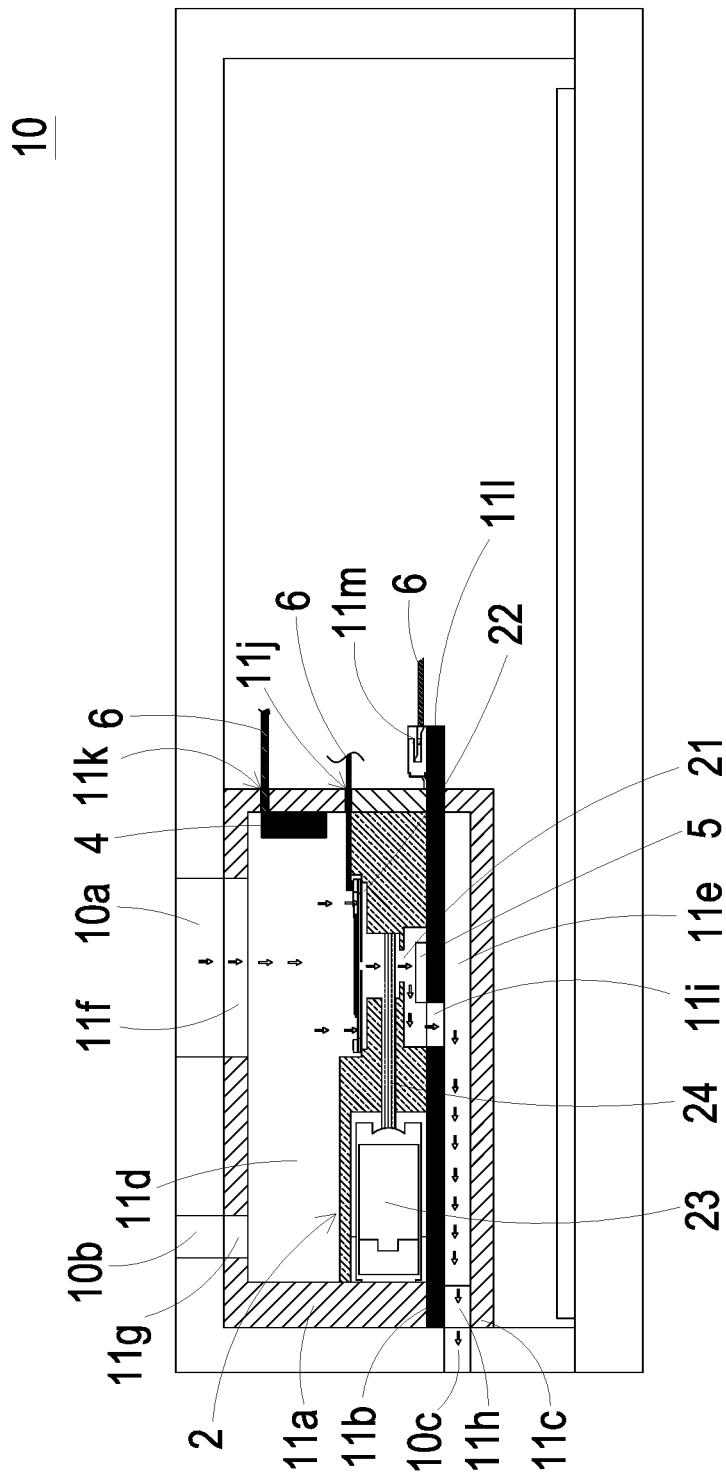
FIG. 2A is a schematic cross-sectional view illustrating a particle detecting module applied to a slim portable device according to an embodiment of the present disclosure.
Figure 2B:
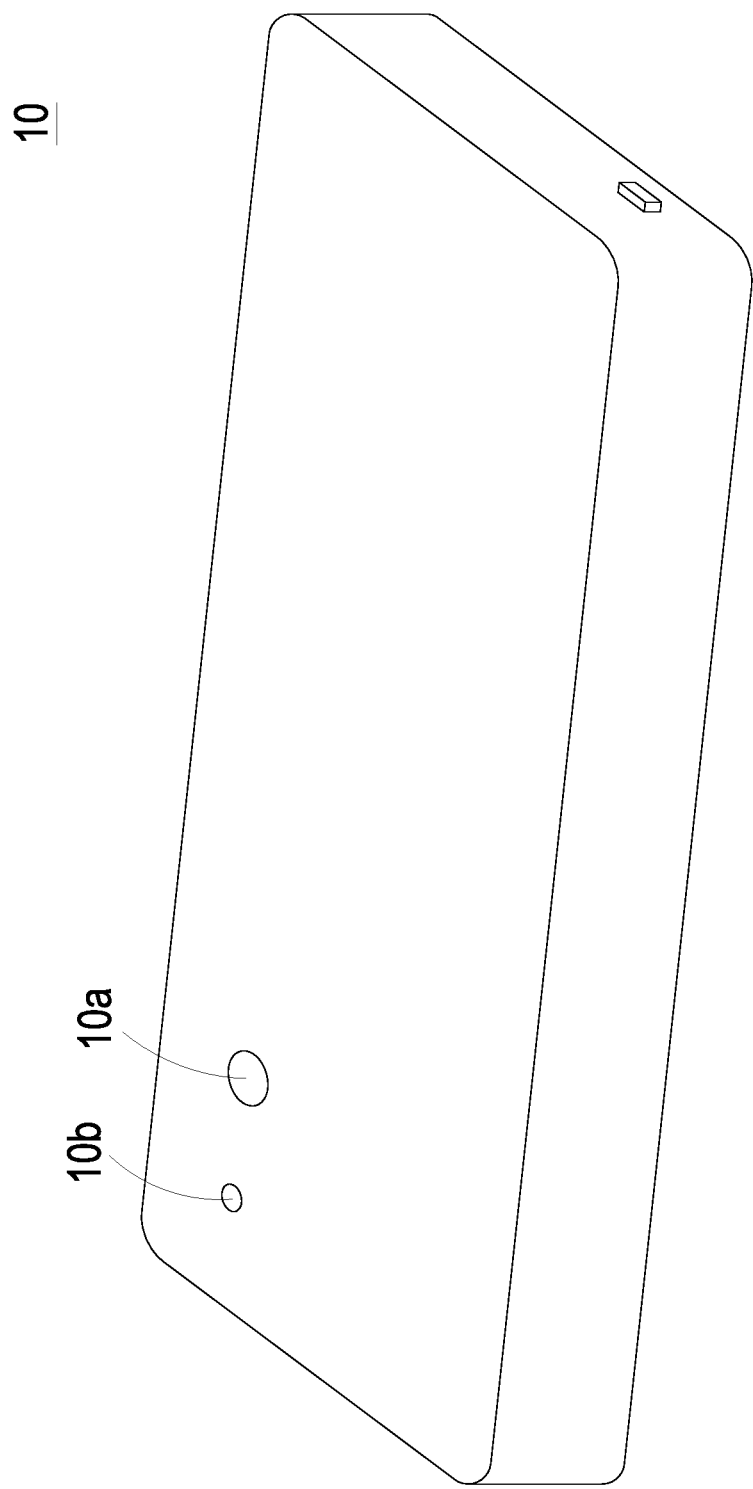
FIG. 2B is a schematic exterior view illustrating a particle detecting module applied to a slim portable device according to an embodiment of the present disclosure.
Figure 2C:
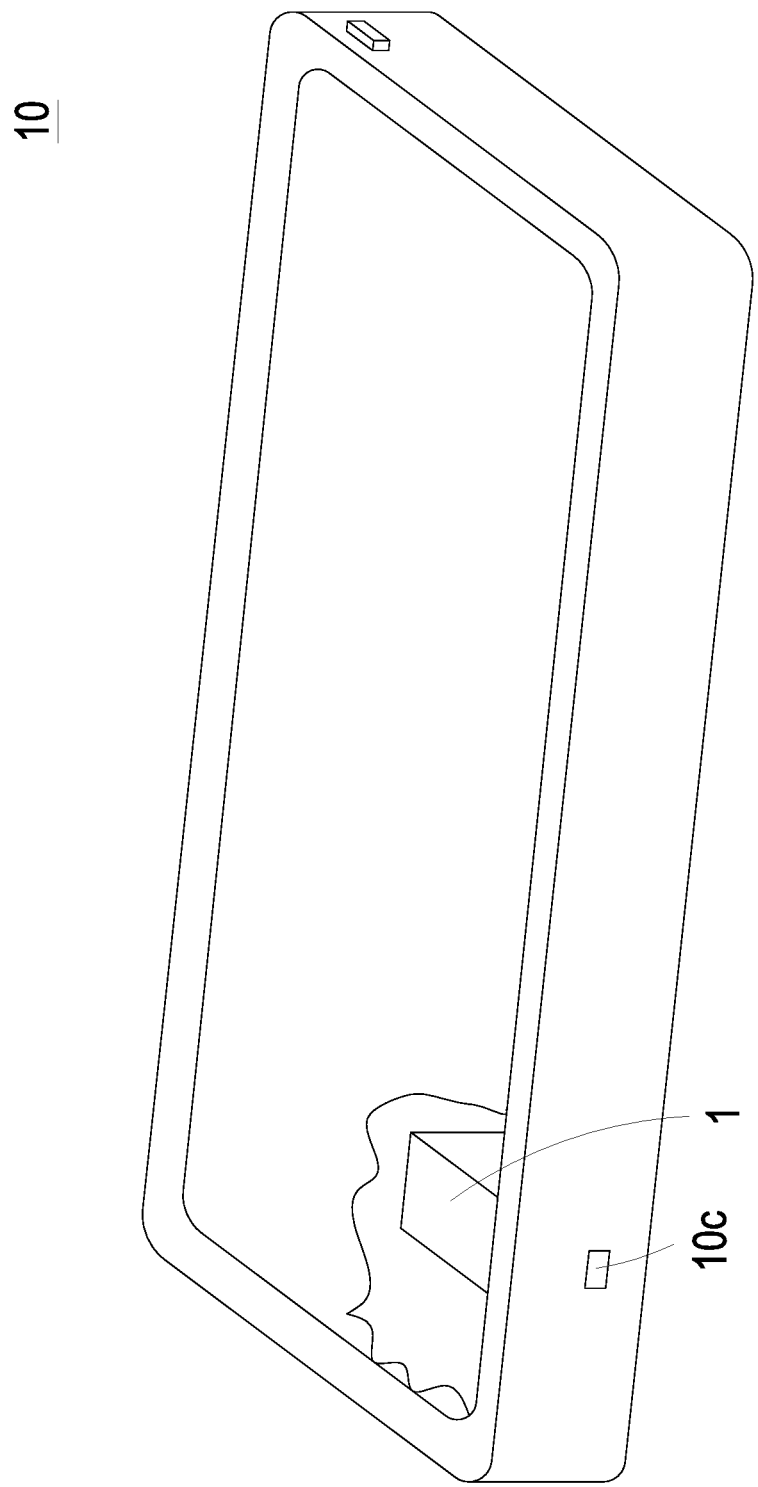
FIG. 2C is another schematic exterior view illustrating a particle detecting module applied to a slim portable device according to an embodiment of the present disclosure.
Figure 3:
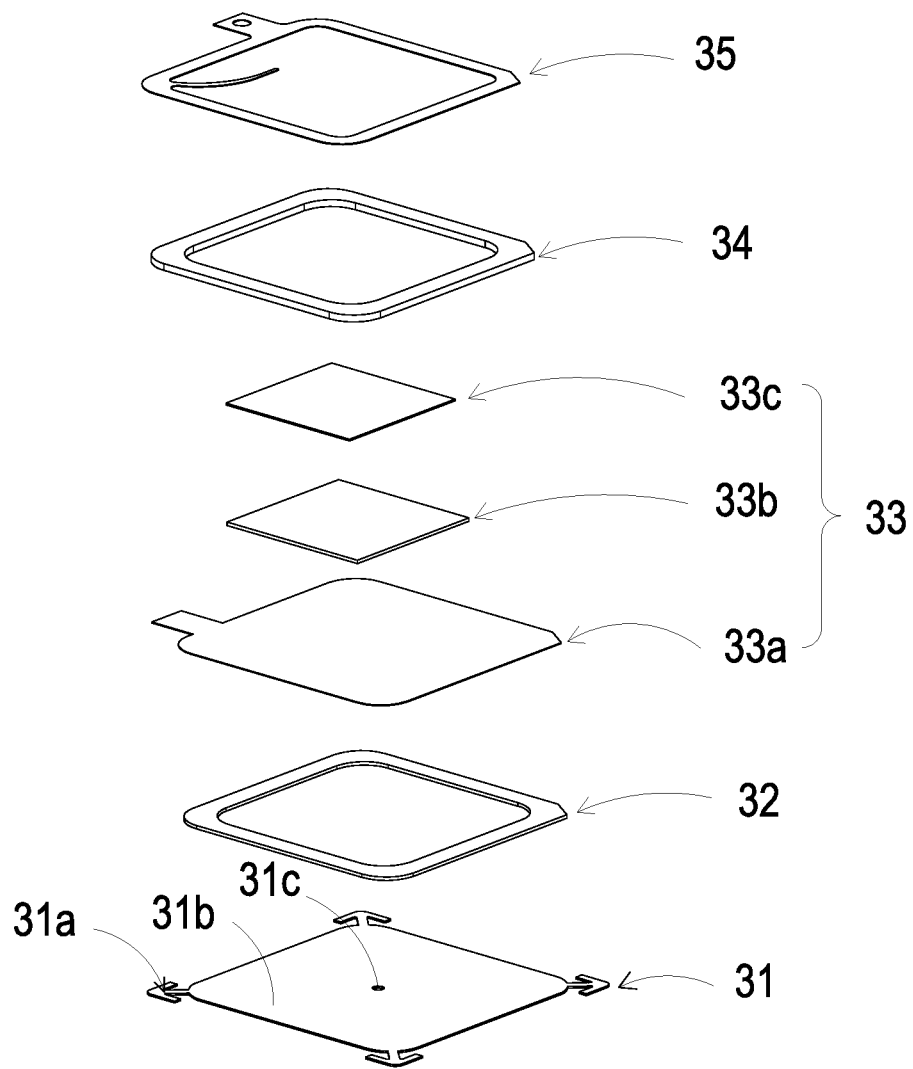
FIG. 3 is an exploded view illustrating an actuator of the particle detecting module according to an embodiment of the present disclosure.

Please refer to FIGS. 2A, 2B and 2C. In some embodiments, the particle detecting module is applied to and assembled within a slim portable device 10. The slim portable device 10 has a first opening 10a, a second opening 10b and a third opening 10c. The particle detecting module is fixed inside the slim portable device 10, as the inlet 11f, the hot gas exhausting opening 11g and the outlet 11h thereof connect and in fluid communication with the first opening 10a, the second opening 10b and the third opening 10c, respectively. When the actuator 3 is actuated, a negative pressure is formed inside the first compartment 11d, so that the gas outside the slim portable device 10 is introduced into the first compartment 11d through the inlet 11f and transported through the communicating opening 11i to the second compartment 11e, and then the gas in the second compartment 11e is discharged through the outlet 11h as being driven by actuation of the actuator 3, thereby achieving single-direction gas transportation for gas monitoring.

The actuating and sensing module of the present disclosure can isolate interference, such as the heat generated by the internal actuators or other waste heat and gas pollution existing within the slim portable device 10, from affecting detection of the sensor 5. Moreover, through the utilization of the actuator 3, one-way gas transportation for introducing and discharging gas is provided, which accelerates the process of transporting gas to a surface of the sensor 5 and thereby enhancing the detecting efficiency of the sensor 5. Also, since it is the gas outside the slim portable device 10 that is transported to the actuating and sensing module, the characteristic of the gas to be monitored by and is inhaled within the actuating and sensing module is the same as the characteristic of the gas outside the slim portable device 10, which make the detecting results more precisely. In addition, the heat generated by the heater 4 is isolated by the first body 11a, thereby avoiding the heat generated by the heater 4 from affecting the operations of the components inside the slim portable device 10.

The structure and the actions of the actuator according to one embodiment are described as below.

Please refer to FIGS. 3, 4A, 4B and 4C. The actuator 3 may be a gas pump. The actuator 3 includes a nozzle plate 31, a chamber frame 32, an actuating body 33, an insulation frame 34 and a conducting frame 35 stacked on each other sequentially. The nozzle plate 31 includes a plurality of brackets 31a, a suspension plate 31b and a central aperture 31c. The suspension plate 31b is permitted to undergo a bending vibration. The plurality of brackets 31a are connected to the periphery of the suspension plate 31b. In the embodiment, there are four brackets 31a, which are connected to four corners of the suspension plate 31b, respectively, but the present disclosure is not limited thereto. The central aperture 31c is formed at a central position of the suspension plate 31b. The chamber frame 32 is stacked on the suspension plate 31b. The actuating body 33 is stacked on the chamber frame 32. The actuating body 33 includes a piezoelectric carrying plate 33a, an adjusting resonance plate 33b and a piezoelectric plate 33c. The piezoelectric carrying plate 33a is stacked on the chamber frame 32. The adjusting resonance plate 33b is stacked on the piezoelectric carrying plate 33a. The piezoelectric plate 33c is stacked on the adjusting resonance plate 33b. The piezoelectric plate 33c is configured to drive the piezoelectric carrying plate 33a and the adjusting resonance plate 33b to bend and vibrate in the reciprocating manner in response to the applied voltage and the deformation thereof. The insulation frame 34 is stacked on the piezoelectric carrying plate 33a of the actuating body 33. The conducting frame 35 is stacked on the insulation frame 34. A resonance chamber 36 is formed among the actuating body 33, the chamber frame 32 and the suspension plate 31b. The adjusting resonance plate 33b is thicker than the piezoelectric carrying plate 33a.

Figure 4A:
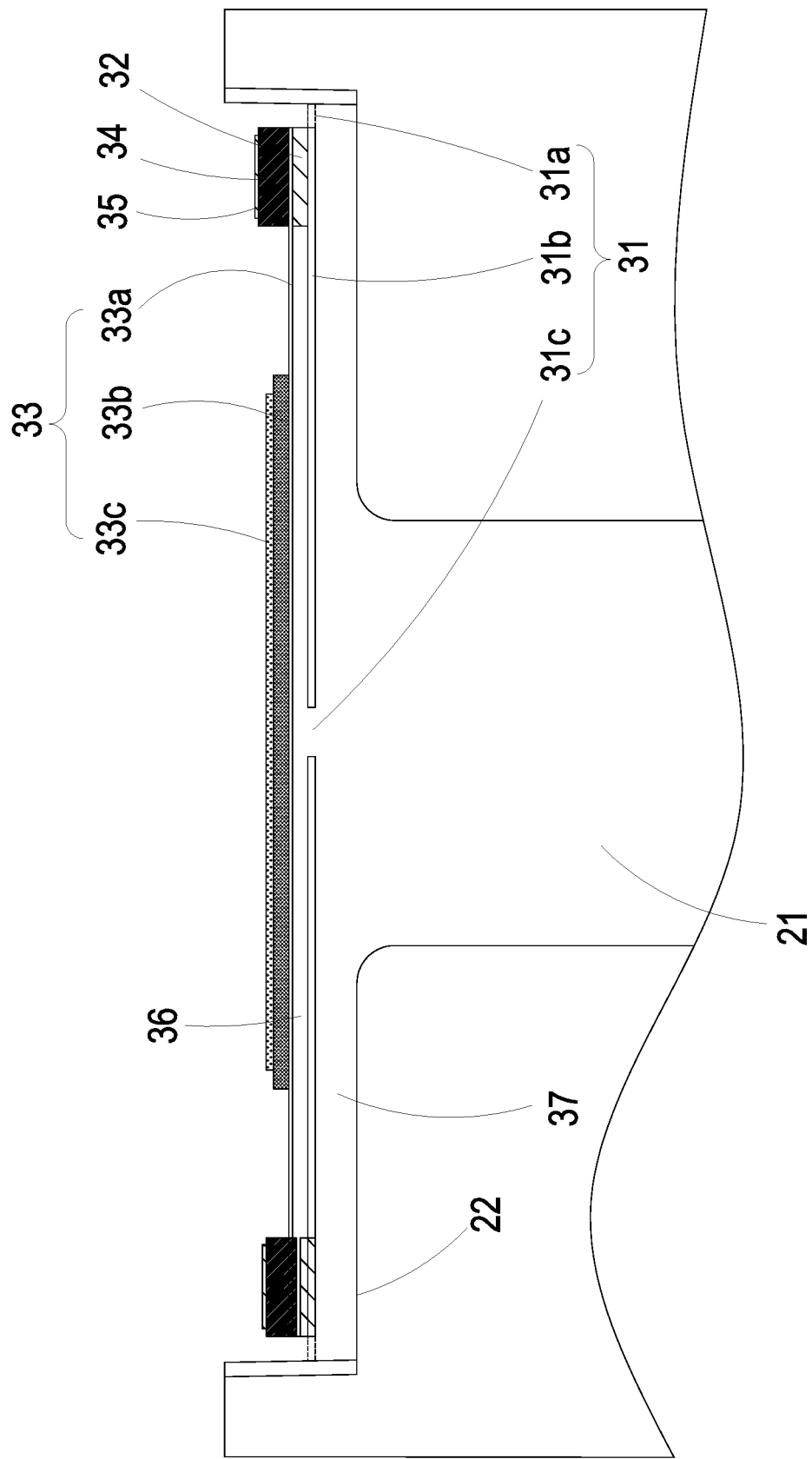
FIG. 4A is a schematic cross-sectional view illustrating the actuator of the particle detecting module according to an embodiment of the present disclosure.
Figure 4B:
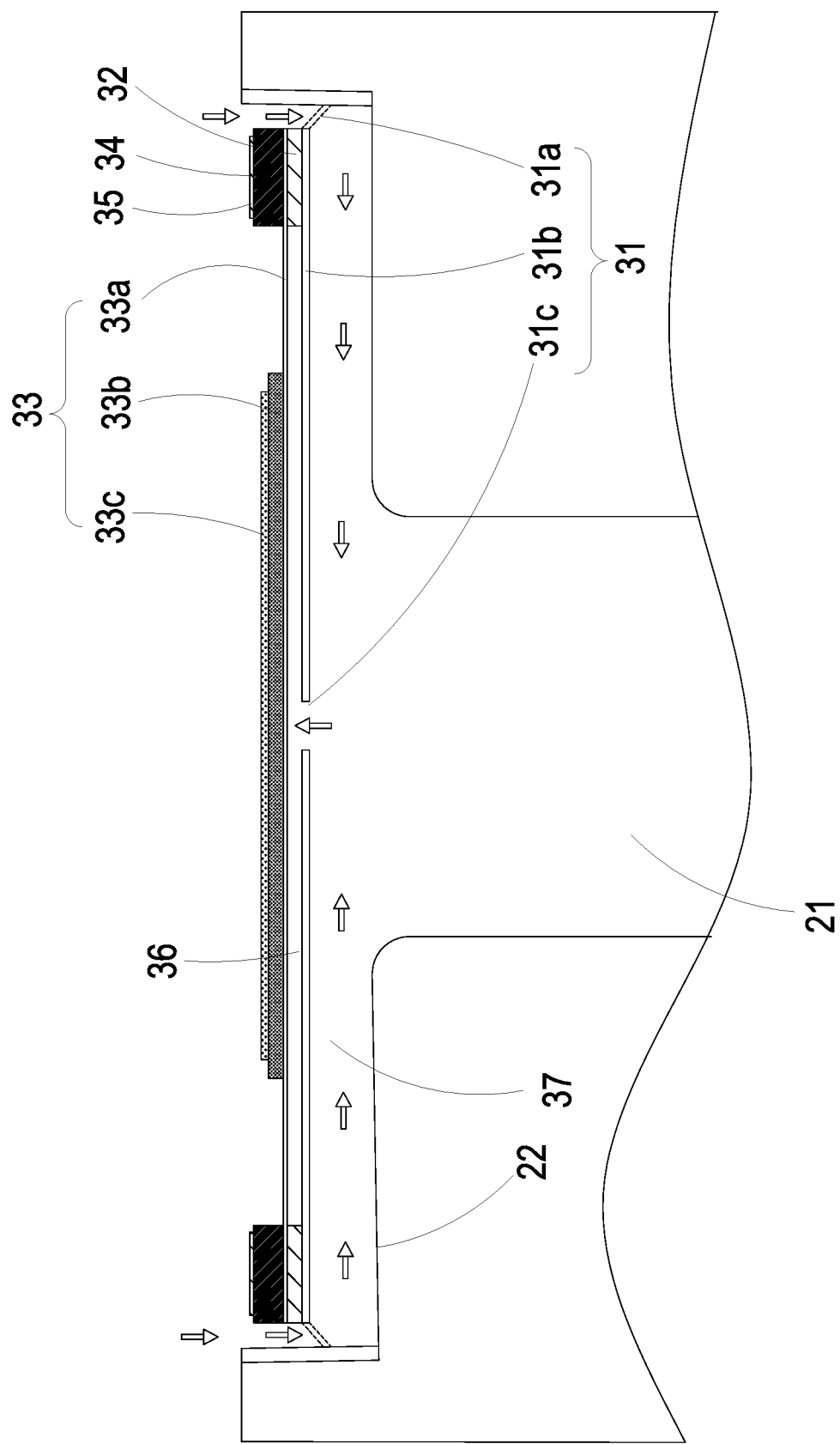
FIG. 4B to FIG. 4C are schematic views illustrating the actions of the actuator of the particle detecting module according to an embodiment of the present disclosure.
Figure 4C:
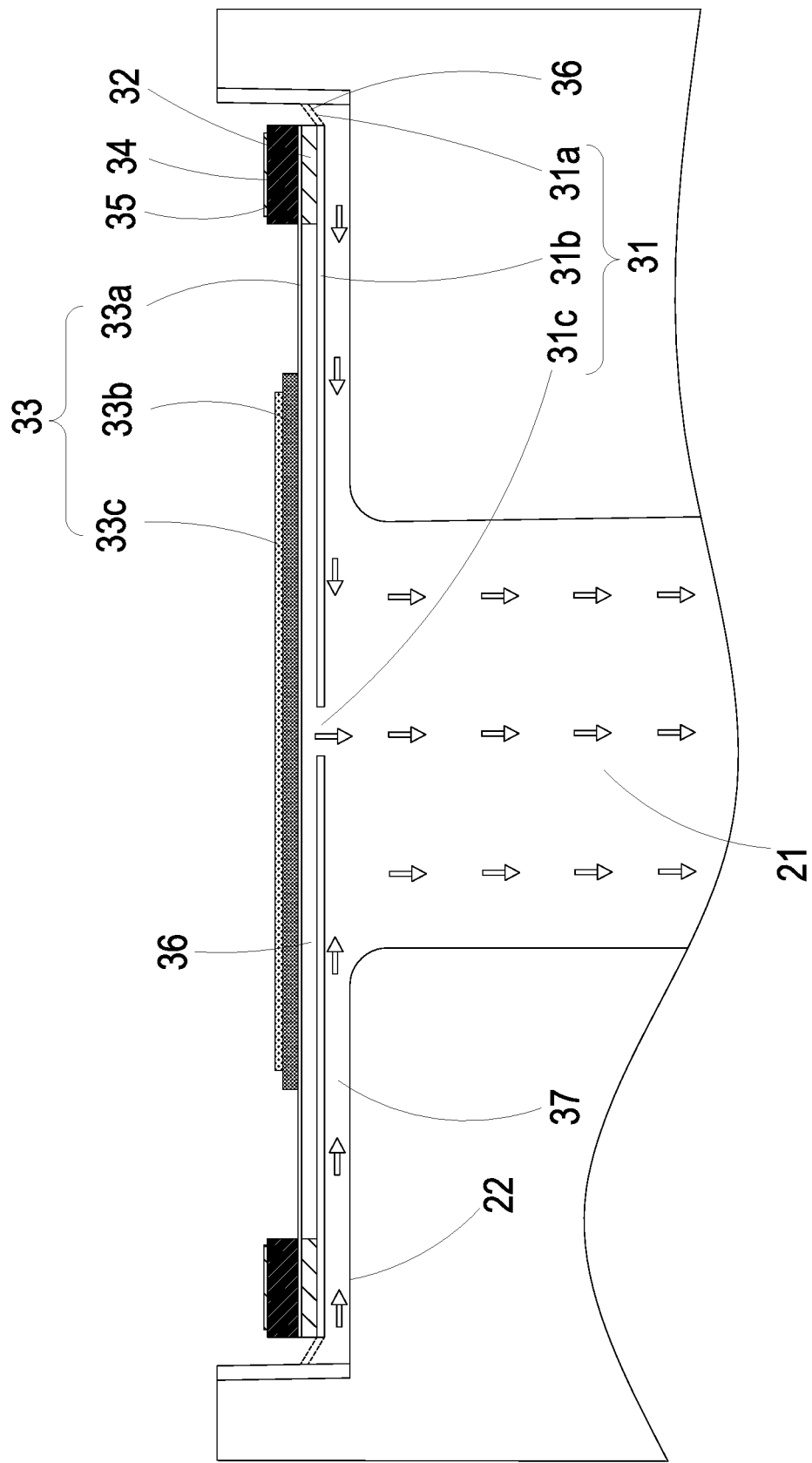

Please refer to FIGS. 4A, 4B and 4C. FIG. 4B to FIG. 4C are schematic views illustrating the actions of an actuator of a particle detecting module according to an embodiment of the present disclosure. Please refer to FIG. 4A firstly. The actuator 3 is disposed within the accommodating recess 22 of the particle monitoring base 2 as being elastically supported by the plurality of brackets 31a, while the nozzle plate 31 is spaced apart from the bottom of the accommodating recess 22 to make an airflow chamber 37 formed between the nozzle plate 31 and the accommodating recess 22. Please refer to FIG. 4B again. When the piezoelectric plate 33c of the actuating body 33 is actuated by an applied voltage, the piezoelectric plate 33c of the actuating body 33 is deformed by the piezoelectric effect, and the adjusting resonance plate 33b and the piezoelectric carrying plate 33a are simultaneously driven to vibrate. Thereby, the nozzle plate 31 is driven to move due to the Helmholtz resonance effect, and the actuating body 33 is displaced in a direction away from the bottom of the accommodating recess 22. As so, the volume of the airflow chamber 37 between the nozzle plate 31 and the bottom of the accommodating recess 22 is expanded, and a negative pressure is formed in the airflow chamber 37. The gas outside the actuator 3 is transported into the chamber 37 through the vacant spaces formed among the brackets 31a of the nozzle plate 31 and the sidewall of the accommodating recess 22 due to the pressure gradient, whereby the airflow chamber 37 is pressurized. Finally, please refer to FIG. 4C. The gas continuously flows into the airflow chamber 37 and a positive pressure is formed in the airflow chamber 37. At this time, the actuating body 33 is driven to displace in a direction toward the bottom of the accommodating recess 22, so that the volume of the airflow chamber 37 is shrunken and the gas inside the airflow chamber 37 is compressed to flow into the monitoring channel 21. Consequently, the gas is provided to the sensor 5, and the sensor 5 can measure the gas to detect the concentration of the suspended particles contained therein.

In the above embodiment, the actuator 3 is a gas pump. In some other embodiments, the actuator 3 of the present disclosure may be a micro-electromechanical-systems gas pump formed by a micro-electromechanical-systems method. The nozzle plate 31, the chamber frame 32, the actuating body 33, the insulation frame 34 and the conducting frame 35 can all be made through a surface micromachining technology to reduce the volume of the actuator 3.

Figure 5:
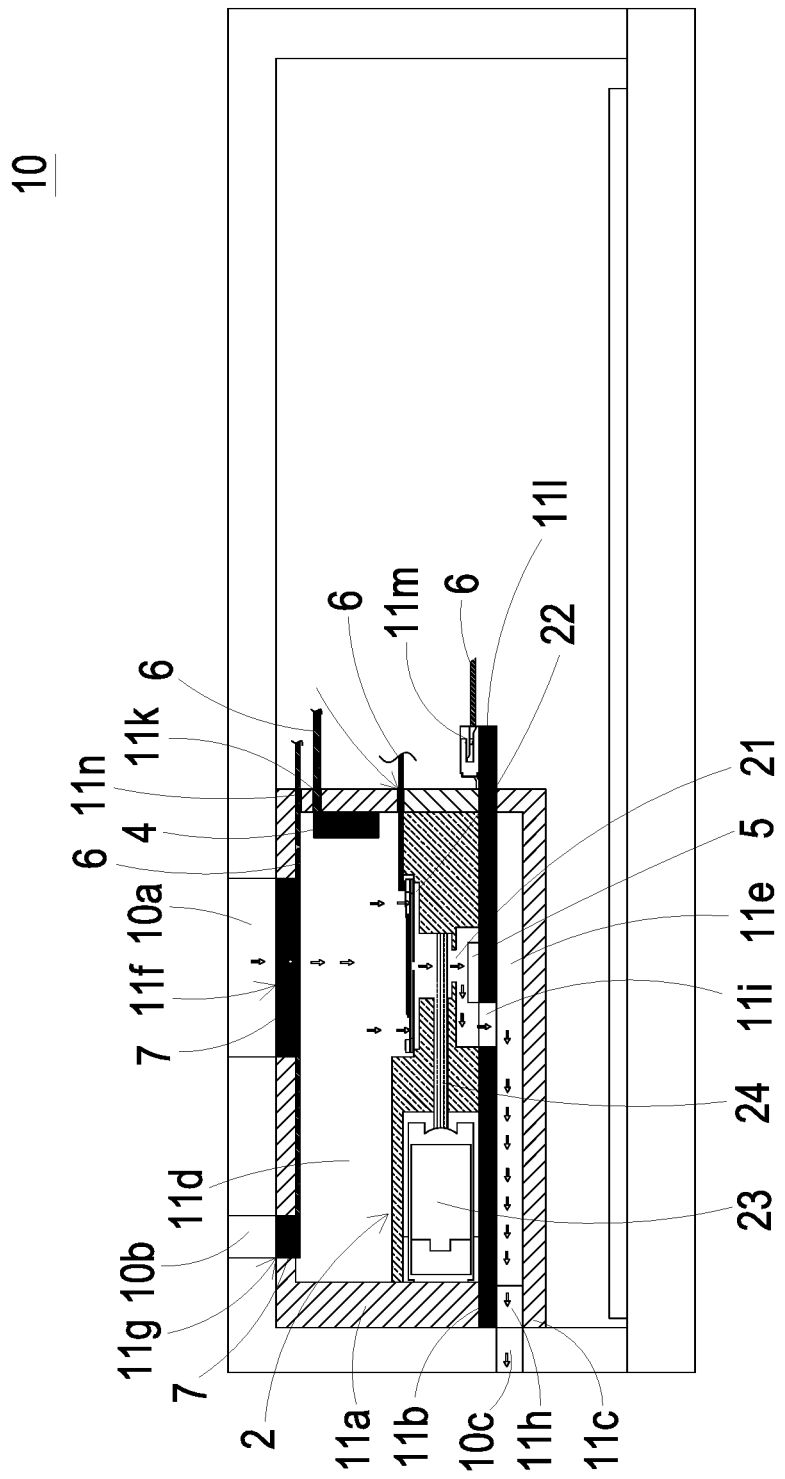
FIG. 5 is a schematic view illustrating a particle detecting module applied to a slim portable device according to another embodiment of the present disclosure.

The particle detecting module may further include at least one valve 7. Please refer to FIG. 5. In one embodiment of the present disclosure, the actuating and sensing module has two valves 7 respectively disposed at the inlet 11f and the hot gas exhausting opening 11g to control each of the inlet 11f and the hot gas exhausting opening 11g to be selectively opened or closed. More specifically, when the humidity inside the first compartment 11d is at a level higher than the monitor standard level, the valve 7 disposed at the hot gas exhausting opening 11g is opened and the heater 4 is actuated, thereby removing moisture in the gas and discharging the water vapor generated thereby out from the first compartment 11d through the hot gas exhausting opening 11g. As a result, the humidity inside the first compartment 11d is reduced. Oppositely, once the humidity inside the first compartment 11d has reached the monitor standard level, the valve 7 disposed at the hot gas exhausting opening 11g is closed to keep the humidity of the gas within the first compartment 11d maintaining at the monitor standard level, thereby enhancing the efficiency of monitoring the suspended particles. In addition, by utilizing the valves 7 to close the inlet 11f and the hot gas exhausting opening 11g and isolating the affections caused by external factors towards the interior of the particle detecting module with the first body 11a and the second body 11b, the accuracy of monitoring the suspended particles is ensured. In addition, the first body 11a further includes a third connecting perforation 11n provided for the flexible circuit board 6 to penetrate therethrough and connect to a plurality of valves 7 for controlling the valves 7. After connecting the flexible circuit board 6 to the plurality of valves 7, the third connecting perforation 11n is sealed by a potting compound to prevent gas from flowing into the first compartment 11d therethrough.

Figure 6A:
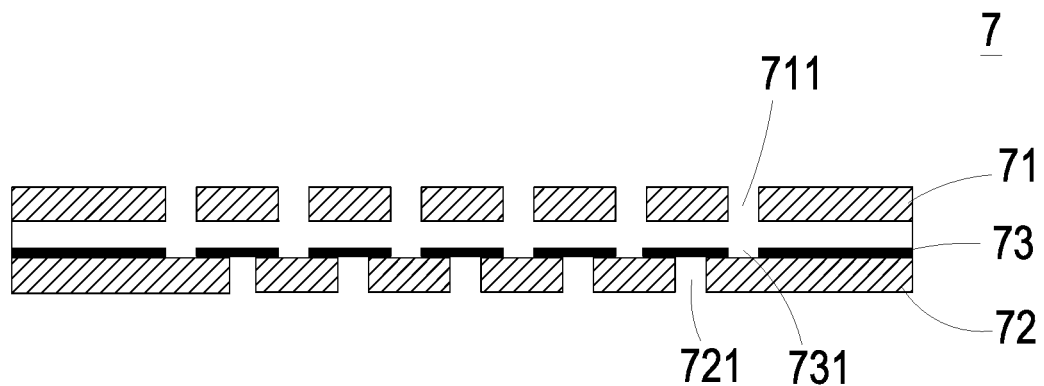
FIG. 6A is a schematic cross-sectional view illustrating the valves of FIG. 5.
Figure 6B:
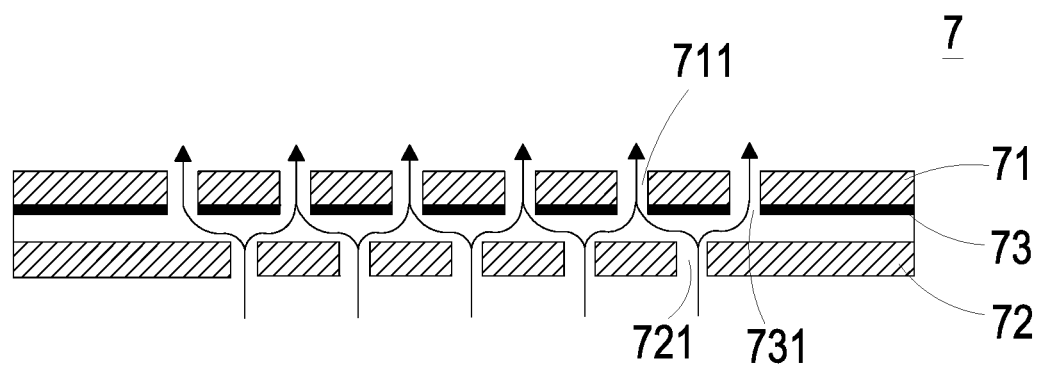
FIG. 6B is a schematic view illustrating the actions of the valves of FIG. 6A.

In some embodiments, referring now to FIG. 6A and FIG. 6B, the valve 7 includes a stationary component 71, a sealing component 72 and a displacement component 73. The displacement component 73 is disposed between the stationary component 71 and the sealing component 72. The stationary component 71 has a plurality of first orifices 711. The displacement component 73 has a plurality of second orifices 731 respectively aligned with the plurality of first orifices 711 of the stationary component 71. The sealing component 72 has a plurality of third orifices 721 misaligned with the plurality of first orifices 711 of the stationary component 71. The stationary component 71, the sealing component 72 and the displacement component 73 of the valve 7 are connected with a processor (not shown) through the flexible circuit board 6. Under control of the processor, the displacement component 73 is moved toward the stationary component 71 so that the valve 7 is in an open state.

In a first aspect of the valve 7 in the present disclosure, the displacement component 73 of the valve 7 described above is made of a charged material, and the stationary component 71 is made of a bipolar conductive material. The stationary component 71 is electrically connected with the processor of the flexible circuit board 6 for controlling the polarity (positive electrical polarity or negative electrical polarity) of the stationary component 71. In case that the displacement component 73 is made of a negative-charged material, the stationary component 71 is controlled to form a positive electrode when the valve 7 has to be controlled to open. As a result, the displacement component 73 and the stationary component 71 are controlled to maintain in opposite polarities, the displacement component 73 moves toward the stationary component 71 so that the valve 7 is in an open state (as shown in FIG. 6B). On the other hand, in case that the displacement component 73 is made of a negative-charged material, the stationary component 71 is controlled to form a negative electrode when the valve 7 has to be controlled to close. As a result, the displacement component 73 and the stationary component 71 are controlled to maintain in the same polarity, the displacement component 73 moves toward the sealing component 72 so that the valve 7 is in a closed state (as shown in FIG. 6A).

In a second aspect of the valve 7 in the present disclosure, the displacement component 73 is made of a magnetic material, and the stationary component 71 is made of an electromagnet material and can be controlled to change its magnetic polarity. The stationary component 71 is electrically connected with the processor of the flexible circuit board 6 for controlling the polarity (positive magnetic polarity or negative magnetic polarity) of the stationary component 71. In case that the displacement component 73 is made of a negative-magnetic material, the stationary component 71 is controlled to form a positive-magnetic pole when the valve 7 has to be controlled to open. As a result, the displacement component 73 and the stationary component 71 are controlled to maintain in opposite polarities, the displacement component 73 moves toward the stationary component 71 so that the valve 7 is in an open state (as shown in FIG. 6B). On the other hand, in case that the displacement component 73 is made of a negative-magnetic material, the stationary component 71 is controlled to form a negative-magnetic pole when the valve 7 has to be controlled to close. As a result, the displacement component 73 and the stationary component 71 are controlled to maintain the same polarity, the displacement component 73 moves toward the sealing component 72 so that the valve 7 is in a closed state (as shown in FIG. 6A).

In summary, the present disclosure provides a particle detecting module having a heater within the first compartment to maintain a monitor standard level of humidity in the first compartment, and guiding the gas at the monitor standard level in the first compartment to the monitoring channel by the actuator, thereby detecting the sizes and a concentration of the particles contained in the gas. Since the humidity of the gas to be detected is maintained at the monitor standard level, the efficiency of particle detection by the sensor is enhanced. Moreover, the particle detecting module of the present disclosure is suitably combined with a slim portable device to use, so that the object of detecting suspended particles at anytime and anywhere is achieved.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A particle detecting module, comprising:
   a main body comprising a supporting partition plate, an inlet, a hot gas exhausting opening and an outlet, wherein an interior of the main body is divided into a first compartment and a second compartment by the supporting partition plate, the inlet and the hot gas exhausting opening are in fluid communication with the first compartment, the outlet is in fluid communication with the second compartment, and the supporting partition plate has a communicating opening in fluid communication between the first compartment and the second compartment;
   a particle monitoring base disposed within the first compartment and comprising a monitoring channel having an accommodating recess at one end thereof and in fluid communication with the monitoring channel;
   an actuator disposed within the accommodating recess of the particle monitoring base and configured to control gas to be introduced into the first compartment through the inlet, transported to the second compartment through the communicating opening, and discharged out through the outlet, thereby achieving single-direction gas transportation;
   a heater disposed within the first compartment and heating the first compartment to maintain a monitor standard level of humidity in the first compartment; and
   a sensor disposed adjacent to the supporting partition plate and located in the monitoring channel of the particle monitoring base, thereby monitoring the gas guided into the monitoring channel.

2. The particle detecting module according to claim 1, wherein the main body comprises a first body and a second body oppositely connected to each other, and the supporting partition plate is disposed between the first body and the second body, so that the first compartment is formed by the first body and the supporting partition plate, and the second compartment is formed by the second body and the supporting partition plate, wherein the inlet and the hot gas exhausting opening are disposed between the first body and the supporting partition plate and in fluid communication with the first compartment, the outlet is disposed between the second body and the supporting partition plate and in fluid communication with the second compartment, and water vapor generated as a result of heating the first compartment by the heater is exhausted through the hot gas exhausting opening.

3. The particle detecting module according to claim 1, wherein the monitor standard level of humidity is in a range between 10% and 40%.

4. The particle detecting module according to claim 1, wherein the monitor standard level of humidity is in a range between 20% and 30%.

5. The particle detecting module according to claim 1, wherein the sensor is a PM 2.5 sensor.

6. The particle detecting module according to claim 1, wherein the actuator is a micro-electromechanical-systems gas pump.

7. The particle detecting module according to claim 1, wherein the actuator is a gas pump, comprising:
   a nozzle plate having a plurality of brackets, a suspension plate and a central aperture, wherein the suspension plate is permitted to undergo a bending vibration, the plurality of brackets are connected to a periphery of the suspension plate, and the central aperture is formed at a central position of the suspension plate, wherein the nozzle plate is disposed within the accommodating recess of the particle monitoring base as being elastically supported by the plurality of brackets and an airflow chamber is formed between the nozzle plate and the accommodating recess, wherein at least one vacant space is formed among the plurality of brackets and the suspension plate;
   a chamber frame carried and stacked on the suspension plate;
   an actuating body carried and stacked on the chamber frame, wherein the actuating body is configured to bend and vibrate in a reciprocating manner in response to an applied voltage, and the actuating body comprises:
      a piezoelectric carrying plate carried and stacked on the chamber frame;
      an adjusting resonance plate carried and stacked on the piezoelectric carrying plate, wherein the adjusting resonance plate is thicker than the piezoelectric carrying plate; and
      a piezoelectric plate carried and stacked on the adjusting resonance plate, wherein the piezoelectric plate is configured to drive the piezoelectric carrying plate and the adjusting resonance plate to bend and vibrate in the reciprocating manner in response to the applied voltage;
   an insulation frame carried and stacked on the actuating body; and
   a conducting frame carried and stacked on the insulation frame;
   wherein a resonance chamber is formed among the actuating body, the chamber frame and the suspension plate, wherein when the actuating body is actuated, a resonance of the nozzle plate occurs so that the suspension plate thereof is driven to vibrate and displace in a reciprocating manner, thereby making the gas flow through the at least one vacant space into the airflow chamber and then exhaust through the monitoring channel to achieve transportation of the gas.

8. The particle detecting module according to claim 1, wherein the supporting partition plate is a circuit board, and the particle monitoring base and the sensor are electrically connected to the supporting partition plate, wherein the particle monitoring base comprises a laser electrically connected to the supporting partition plate and a beam channel perpendicularly in communication with the monitoring channel, wherein a laser beam emitted by the laser is illuminated to the monitoring channel, so that suspended particles of the gas inside the monitoring channel are illuminated to generate light points projected on the sensor for detection, wherein the supporting partition plate has an exposed portion penetrating through the main body to the exterior of the main body, and the exposed portion has a connector allowing a flexible circuit board to be penetrated therethrough so as to connect with the supporting partition plate to provide electric connection and signal connection.

9. The particle detecting module according to claim 2, wherein the first body has a first connecting perforation allowing a flexible circuit board to penetrate therethrough and connect to the actuator, after which the first connecting perforation is sealed by a potting compound to prevent an exterior gas from flowing into the first compartment therethrough.

10. The particle detecting module according to claim 2, wherein the first body has a second connecting perforation allowing a flexible circuit board to penetrate therethrough and connect to the heater, after which the second connecting perforation is sealed by a potting compound to prevent an exterior gas from flowing into the first compartment therethrough.

11. The particle detecting module according to claim 2, wherein the first body has a third connecting perforation allowing a flexible circuit board to penetrate therethrough and connect to a plurality of valves, after which the third connecting perforation is sealed by a potting compound to prevent an exterior gas from flowing into the first compartment therethrough.

12. The particle detecting module according to claim 11, wherein the plurality of valves are respectively disposed at the inlet and the hot gas exhausting opening, and each of the valves comprises a stationary component, a sealing component and a displacement component, wherein the displacement component is disposed between the stationary component and the sealing component, the stationary component has a plurality of first orifices, the displacement component has a plurality of second orifices, and the sealing component has a plurality of third orifices, wherein the plurality of the first orifices of the stationary component are aligned with the plurality of the second orifices of the displacement component, and the plurality of the third orifices of the sealing component are misaligned with the plurality of the first orifices of the stationary component, and wherein the displacement component is controlled to move toward the stationary component by a processor, so that the valve is in an open state.

13. A particle detecting module, comprising:
  at least one main body, wherein at least one interior of the main body is divided into at least one first compartment and at least one second compartment by at least one supporting partition plate, the main body has at least one inlet, at least one hot gas exhausting opening and at least one outlet, the inlet and the hot gas exhausting opening are in fluid communication with the first compartment, the outlet is in fluid communication with the second compartment, and the supporting partition plate has at least one communicating opening in fluid communication between the first compartment and the second compartment;
  at least one particle monitoring base disposed within the first compartment and comprising at least one monitoring channel having at least one accommodating recess at one end thereof and in fluid communication with the monitoring channel;
  at least one actuator disposed within the accommodating recess of the particle monitoring base and configured to control gas to be introduced into the first compartment through the inlet, transported to the second compartment through the communicating opening, and discharged out through the outlet, thereby achieving single-direction gas transportation;
  at least one heater disposed within the first compartment and heating the first compartment to maintain at least one monitor standard level of humidity in the first compartment; and
  at least one sensor disposed adjacent to the supporting partition plate and located in the monitoring channel of the particle monitoring base, thereby monitoring the gas guided into the monitoring channel.

* * * * *